United States Patent
Nagasaki et al.

(10) Patent No.: US 6,590,043 B1
(45) Date of Patent: Jul. 8, 2003

(54) METHACRYLIC POLYMER HAVING A TERMINAL FUNCTIONAL GROUP AND COMPOSITION THEREOF

(75) Inventors: Yukio Nagasaki, Kitasoma-gun (JP); Masao Kato, Tsukuba (JP); Kazunori Kataoka, Kashiwa (JP); Yasuo Sato, Inashiki-gun (JP); Atsushi Harada, Matsudo (JP); Daisuke Wakebayashi, Noda (JP)

(73) Assignee: Nano Carrier Co., Ltd., Chiba-ken (JP)

( * ) Notice: Subject to any disclaimer, the term of this patent is extended or adjusted under 35 U.S.C. 154(b) by 0 days.

(21) Appl. No.: 09/402,879

(22) PCT Filed: Apr. 8, 1998

(86) PCT No.: PCT/JP98/01599

§ 371 (c)(1),
(2), (4) Date: Dec. 21, 1999

(87) PCT Pub. No.: WO98/46655

PCT Pub. Date: Oct. 22, 1998

(30) Foreign Application Priority Data

Apr. 14, 1997 (JP) ............................................. 9-110044

(51) Int. Cl.⁷ ............................ C08F 20/34; C08F 4/08; C08G 63/08; C08G 63/685; C08G 63/91; C08G 65/32
(52) U.S. Cl. ........................................ 525/404; 526/212
(58) Field of Search ........................... 525/404; 526/212

(56) References Cited

U.S. PATENT DOCUMENTS 4,056,559 A   11/1977   Lewis et al.
4,103,093 A * 7/1978   Lewis et al. ................. 526/212

FOREIGN PATENT DOCUMENTS

| EP | 465835   | 1/1992  |
|----|----------|---------|
| JP | 435756   | 3/1968  |
| JP | 4722330  | 6/1972  |
| JP | 61250011 | 11/1986 |
| JP | 04041515 | 2/1992  |
| JP | 04323204 | 11/1992 |
| JP | 07258361 | 10/1995 |
| JP | 09208628 | 8/1997  |

OTHER PUBLICATIONS

Mukhitdinova, N.A., et al. "Polymerization of N,N–diethylamino–ethyl methacrylate in the presence of anionic catalysts" Chemical Abstracts 79:53858.

Nagasakai, Y., et al. A novel synthesis of semitelechelic functional poly(methacrylate)s through an alcoholate, etc. Macromelecular Rapid Communications, Wiley, V. 18, Nr. 9, pp. 827–835.

* cited by examiner

*Primary Examiner*—D. R. Wilson
(74) *Attorney, Agent, or Firm*—Sherman & Shalloway

(57) ABSTRACT

The present invention provides a polymer obtained by polymerizing a mixture composed of a methacrylic ester monomer having an electron-donating group bonded to a specific site of its ester-forming residue (its alcohol moiety) and optionally a lactone or lactide, while using an alkali metal alcoholate as a polymerization initiator. Moreover, it also provides a process for preparing the polymer and polymer micelles formed from the polymer. Since the polymer has a functional group corresponding to the polymerization initiator and the aforesaid electron-donating groups (functional groups), it can perform a great variety of functions by taking advantage of these functional groups.

9 Claims, 6 Drawing Sheets

(a)

(b)

(c)

Eluted volume (ml)

METHACRYLIC POLYMER HAVING A TERMINAL FUNCTIONAL GROUP AND COMPOSITION THEREOF

TECHNICAL FIELD

This invention relates to polymers which are prepared by living anionic polymerization and which contain a segment derived from a methacrylic ester and having a terminal functional group, a process for preparing the same, and compositions containing such polymers.

BACKGROUND ART

Conventionally, the anionic polymerization of α, β-unsaturated carbonyl compounds, typified by methyl methacrylate (MMA), is important in obtaining polymeric compounds having a controlled molecular weight or a controlled terminus, and has hence been investigated extensively. For example, in the anionic polymerization of MMA, molecular designs have usually been made by using an alkali metal alkyl (e.g., butyllithium or sodium naphthalene) as a living polymerization initiator. However, when an oxonium anion such as an alkali metal alcoholate is used as an initiator, MMA exhibits such low reactivity that, in the existing state of the art, MMA cannot be polymerized without resorting to various means (e.g., the use of a complexing agent such as a crown ether).

In the course of close investigation on the anionic polymerization characteristics of 2-hydroxyethyl methacrylate monomer whose hydroxyl group is protected with a trialkylsilyl group (hereinafter also referred to as ProHEMA), the present inventors have previously found that, in contrast to MMA and the like, this monomer can readily be polymerized with the aid of an alkali metal alcoholate because the monomer itself acts as a complexing agent (see Japanese Patent Laid Open No. 208628/'97). This has made it possible to introduce a greater variety of terminal groups into poly-HEMA, as contrasted with the prior art in which only radical poly-merization has been employed for this purpose, and also to carry out anionic polymerization without using alkali metal alkyls which have very high reactivity in anionic polymerization and are hence difficult to handle.

However, this process is limited to the synthesis of poly-HEMA having hydroxyl groups. As to the preparation of polymeth-acrylic esters having other functional groups, no polymerization process using an alkali metal alcoholate as an initiator has been known as yet.

Accordingly, an object of the present invention is to provide polymers which not only have a functional group at an end of the polymer, but also have any of various functional groups other than trialkylsiloxy groups in the ester residues derived from an MMA ester (i.e., the portions derived from an alcohol).

DISCLOSURE OF THE INVENTION

As a result of close investigation on the mechanism of this anionic polymerization reaction, the present inventors have now found that a methacrylic ester monomer having an electron-donating substituent group bonded to a specific site of its ester residue can be specifically and easily polymerized with the aid of a potassium alcoholate. It has been confirmed that, if a cyclic ether (e.g., ethylene oxide) or a cyclic ester (e.g., a lactide or lactone) is previously reacted with this polymerization system, a living polymer chain is produced correspondingly and the polymer chain of the aforesaid methacrylic ester can be extended through the medium of this living polymer chain. Moreover, it has also been found that, if a cyclic ether (e.g., ethylene oxide) or a cyclic ester (e.g., a lactide or lactone) is allowed to coexist in this reaction system, such a monomer readily undergoes random copolymerization to yield a copolymer of a methacrylic ester having a functional group and a lactide or lactone. These represent new polymerization techniques for the preparation of polymeth-acrylic esters having functional groups at the ester sides, and provide a previously unknown method for the introduction of a terminal functional group.

Thus, according to the present invention, there is provided a polymer represented by the following formula (I) and containing a polymethacrylic ester segment having a terminal functional group.

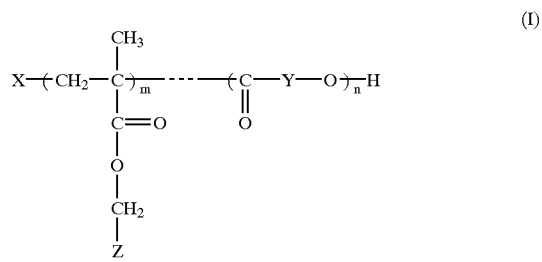

(I)

wherein

X is represented by the group

in which

R$^1$ is an unsubstituted or substituted straight-chain or branched C$_{1-15}$ alkoxy group, an unsubstituted or substituted aryloxy group, or an unsubstituted or substituted aryl-C$_{1-3}$ alkoxy group, and, when R$^1$ is a substituted group, the substituent is a vinyl group, an acetal-forming group, a cyano group, an aldehyde group, a carboxyl group, an amino group, a C 1-6 alkoxycarbonyl group, a C$_{2-7}$ acylamide group, a tri (C$_{1-6}$ alkyl)siloxy group having the same or different alkyl groups, a siloxy group, or a silylamino group, the linkage group —L— is represented by the formula

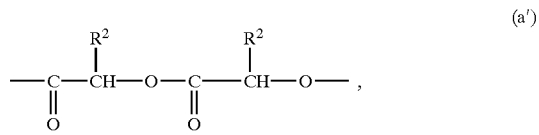

(a')

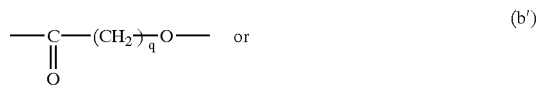

(b')

(c')

in which the R$^2$ groups are the same or different C$_{1-6}$ alkyl groups, q is an integer in the range of 3 to 5, and p is an integer in the range of 0 to 1,000;

Z represents the group

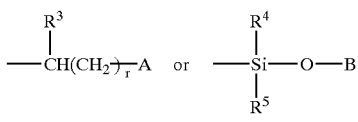

in which $R^3$ is hydrogen or a $C_{1-6}$ alkyl group, A is $NR^6R^7$,

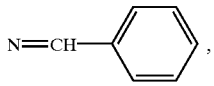

$P(OR^8)_3$, $SR^9$ or SH, r is 0 or 1, $R^6$, $R^7$ and $R^8$ are the same or different $C_{1-6}$ alkyl groups, $R^9$ is a tri($C_{1-6}$ alkyl)silyl group, and B is a $C_{1-6}$ alkyl group;

n is an integer equal to 0 or in the range of 5 to 10,000; and m is a positive number of 5 to 10,000;

provided that the polymer is a random copolymer when n is other than 0.

Such polymers, in themselves, are useful as functional polymers in a wide technical field. Moreover, when the X group contains, for example, an ethylenically unsaturated polymerizable group, they can be used as macromonomers for the preparation of further polymers, or can provide further functional polymers with the aid of other functional groups. In particular, the polymers (i.e., copolymers) of formula (I) in which n is other than 0 contain a biodegradable segment in the polymer chain, they are not only widely useful as biodegradable plastics, but also can provide materials which are very useful as materials for cell technology (e.g., cell culture beds), matrix polymers for drug delivery systems, and the like.

When n is 0,L in the linkage group $-(L-)_p$ is $-CH_2CH_2-O-$, and p is other than 0, the copolymers of formula (I) are block copolymers having a hydrophilic-hydrophobic polymer (or oligomer) segment, and can form polymer micelles, for example, in an aqueous medium. In this case, the core usually consists of segments derived from a methacrylic ester, and the shell usually consists of segments derived from ethylene oxide. Accordingly, the present invention also provides such polymer micelles. These polymer micelles can carry hydrophobic drugs and negatively chargeable compounds (e.g., nucleic acids, anionic proteins and other anionic drugs) in the core thereof, and are hence useful as carriers for the delivery of drugs.

Thus, according of the present invention, there is also provided a polymer micelle composition comprising the aforesaid polymer micelles having a nucleic acid or anionic protein contained therein. Among nucleic acids, those being used as drugs or investigated for use as drugs (e.g., various antisense DNAs) are especially contemplated.

The above-described polymers of formula (I) may be efficiently prepared according to the following preparation process which constitutes another embodiment of the present invention. That is, according to the present invention, there is also provided a process for the preparation of a polymer of formula (II) which comprises the step of polymerizing an alkali metal alcoholate of the formula (II)

$$X-M \quad (II)$$

wherein X is as defined for formula (I) and M is lithium, sodium, potassium, cesium or strontium, with a methacrylic ester of the formula (III)

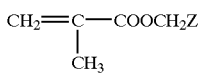

wherein Z is as defined for formula (I), and optionally with a lactone or lactide of the formula (IV)(a) or (b)

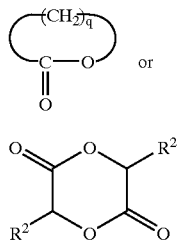

wherein q and $R^2$ are as defined for formula (I), optionally in the presence of an inert solvent.

Conventionally, it has been considered that some MMA esters are scarcely polymerized, or not polymerized at all, by anionic polymerization using a metal alcoholate as a polymerization initiator. Although it is not wished to be bound by theory, the reason why, among such MMA esters, the monomers of formula (IV) can be efficiently polymerized is believed to be that the reactivity of the alcoholate is enhanced, for example, by the complexing of the alkali metal cation of the polymerization initiator with the monomer as shown in the following formula.

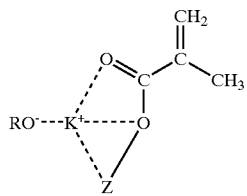

Thus, the polymerization can be made to proceed without using a highly reactive initiator such as butyllithium. Consequently, polymers having various functional groups in the X group and the Z group can be directly prepared.

SPECIFIC DESCRIPTION OF THE INVENTION

Figure 1:
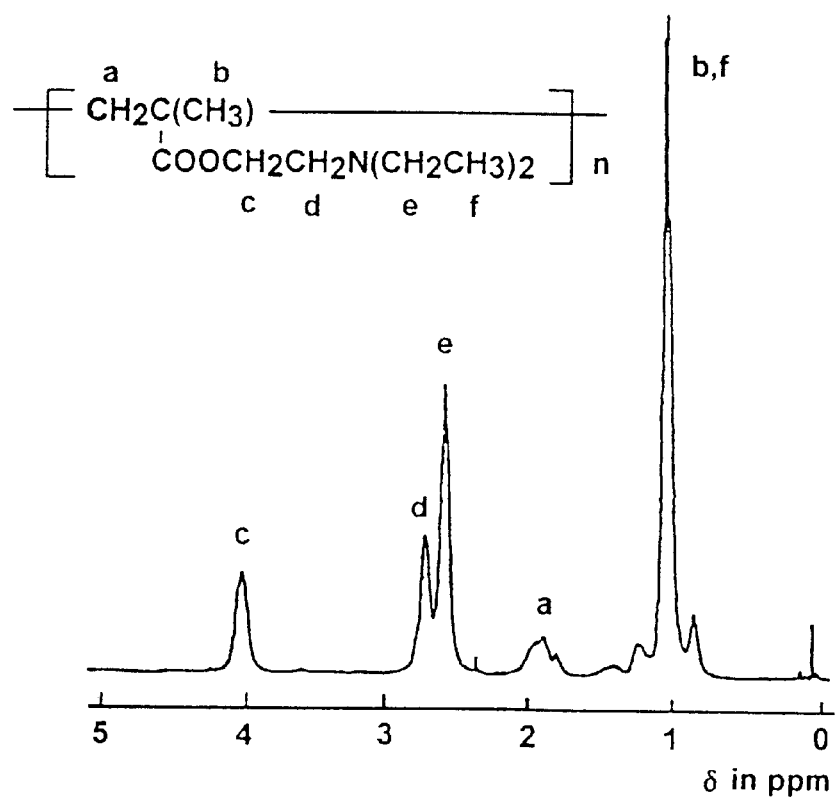
FIG. 1 is an NMR spectrogram of poly(N,N-diethylamino-ethyl methacrylate) prepared by using potassium ethoxide as an initiator.

The X group in formula (I) is a portion originating from a polymerization initiator or a living polymer chain joined to a polymerization initiator portion ($R^1$) derived by-use of a polymerization initiator. Although the X group is preferably a hydrocarbonoxy which is represented by $R^1$ and may be substituted, the X group may be a residue obtained by using its alkali metal alcoholate as a living anionic polymerization initiator to effect the living polymerization of a lactone, lactide or ethylene oxide of the formula (IV) (a'), (b') or (c')

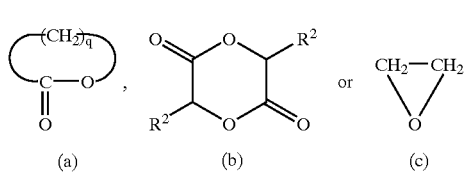

(a)  (b)  (c)

wherein q and $R^2$ are as defined for formula (I).

$R^1$ may be an unsubstituted or substituted group as defined above. However, the groups presenting the features of the present invention are substituted groups.

In the $C_{1-15}$ alkoxy group defined for $R^1$, examples of the alkyl moiety include lower alkyl groups such as methyl, ethyl, propyl, isopropyl, n-butyl, sec-butyl, tert-butyl, n-pentyl and n-hexyl; and higher alkyl groups such as octyl, decyl, undecyl and pentadecyl. In the similarly defined aryloxy group, examples of the aryl moiety include phenyl and naphthyl; and phenyl and naphthyl which are substituted by the above-described lower alkylgroups. Moreover, in the similarly defined aryl-$C_{1-3}$ alkoxy group, examples of the aryl moiety include aryl groups as described for the aforesaid aryloxy group, and examples of the $C_{1-3}$ alkyl moiety include groups derived from methyl, ethyl and propyl.

When the above-described groups further have a substituent, the substituent may comprise a vinyl group, an acetal(forming) group [e.g., two lower alkoxy groups or an α,ω-dioxy(lower alkylene) group], a cyano group, an aldehyde group, a carboxyl group, an amino group, a $C_{1-6}$ alkoxycarbonyl group (examples of the $C_{1-6}$ alkyl moiety include the above-described lower alkyl groups), a $C_{2-7}$ acylamide group (examples of the alkyl moiety of the $C_{2-7}$ acyl group include the above-described lower alkyl groups), a tri($C_{1-6}$ alkyl)siloxy group having the same or different alkyl groups ($R^3SiO$—in which the R groups are the same or different lower alkyl groups), a siloxy group ($H_3SiO$—), a silylamino group ($H_3SiNH$—) or the like.

Furthermore, examples of the $C_{1-6}$ alkyl group present in formula (I) and other various groups described herein include the lower alkyl groups described above for $R^1$.

With respect to the groups

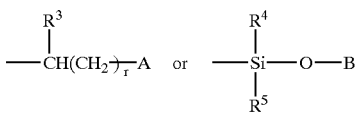

which represent Z in formula (1), the former is preferred and $R^3$ preferably comprises hydrogen. Specific examples of these groups include —$CH_2NR^6R^7$, —$CH_2CH_2NR^6R^7$, —$CH_2$—N=CH—$C_6H_6$, —$CH_2$—P($OR^8$)$_3$, —$CH_2SR^9$ and —$CH_2CH_2SR^9$.

When n in formula (I) is other than 0, the polymer of the present invention is a random copolymercomposed of segments derived from an MMA ester and a lactone or lactide. When n is 0, the polymer of the present invention is a polymer basically consisting of a segment derived from an MMA ester.

According to the polymerization process of the present invention which will be more specifically described later, n and m can be freely chosen by controlling the molar ratio of the polymerization initiator to the monomers.

The polymerization initiator, monomers and reaction conditions employed in the polymerization process of the present invention are as follows.

As the polymerization initiator, there is used an alcoholate represented by the following formula (II)

X—M  (II)

wherein X is preferably one of the groups defined for formula (I), but examples thereof include all groups which exert no adverse influence on the relevant polymerization reaction, and M is an alkali metal such as lithium, sodium, potassium, cesium or strontium, and preferably lithium, sodium or potassium. Such alcoholates may be prepared according to a per se known method. Specifically, they may be prepared by reacting a hydroxy compound containing the group $R^1$ or $R^1$-(L-)$_p$, with an alkali metal hydride, alkali metal alkyl or aryl, alkali, alkali metal amide or the like. When the hydroxy compound contains a group represented by the formula

in which p is an integer other than 0, it can be provided as a living polymer (or oligomer) by polymerizing a lactone, lactide or ethylene oxide corresponding to L while using an alkali metal alcoholate of an alcohol containing the group $R^1$ as a living polymerization initiator.

As the monomer, there is used a compound of the formula (III)

wherein Z is preferably a group as defined for formula (I). However, as described above, Z comprehends all groups that can assume a structure capable of forming a complex with the alkali metal of the polymerization initiator, and specifically all group that keep a definite intermolecular distance from the oxygen atom to which $CH_2Z$ is bonded and that exhibit electron-donating properties.

Moreover, as an optional monomer in accordance with the present invention, there is used a lactone or lactide of the formula (IV) (a) or (b)

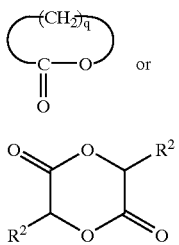

(a)

(b)

wherein q and $R^2$ are as defined for formula (I).

Although the reaction of the above-described polymerization initiator with the monomer(s) may be carried out in the presence or absence of an inert solvent, it is preferably carried out in the presence of an inert solvent. The term "inert solvent" means any solvent that neither exerts an adverse influence on the polymerization reaction or on the initiator and the formed polymer, nor reacts with them. Specific examples of such solvents are liquid solvents which do not react particularly with alkali metal alcoholates under reaction conditions, including ether solvents such as tetrahydrofuran, dioxane, diethyl ether and dimethoxyethane; aromatic hydrocarbons such as benzene, toluene and xylene; aliphatic hydrocarbons such as pentane, hexane, cyclohexane and octane; and aprotic solvents such as dimethyl sulfoxide, N,N-dimethylformamide and hexamethylphosphoric triamide. Among these solvents, ethers such as tetrahydrofuran are most preferred.

The above-described initiator or $R^1\text{-}(L\text{-})=$ may be used in an amount of 0.0001 to 100 moles per mole of the monomer, and the more preferred range is from 0.0001 to 1 mole. The monomer may comprise an MMA ester of formula (III) alone or a mixture of an MMA ester and a lactone or lactide of formula (IV).

The solvent is preferably used in an amount of 0.1 to 1,000 parts by volume, more preferably 0.5 to 100 parts by volume, per part by volume of the monomer. Generally, the reaction becomes slower as the relative amount of the solvent increases.

Although no particular limitation is placed on the temperature at which the polymerization reaction is carried out in the practice of the present invention, it is preferably in the range of −150 to 160° C. and more preferably in the range of −30 to 80° C. Moreover, although no particular limitation is placed on the reaction time, it preferably ranges from 5 seconds to 100 hours and more preferably from 1 minute to 30 minutes. As to the atmosphere for the polymerization reaction, there is used an inert atmosphere of argon, nitrogen gas or the like.

Since the reaction rate may vary according to the reaction conditions and the desired product, it is preferable to determined the reaction time by making a quantitative analysis of the raw materials and the product by gas chromatography, liquid chromatography or the like.

Thus, polymers having a terminal functional group can be prepared. Among the polymers thus obtained, polymers represented by the following formula (I-c)

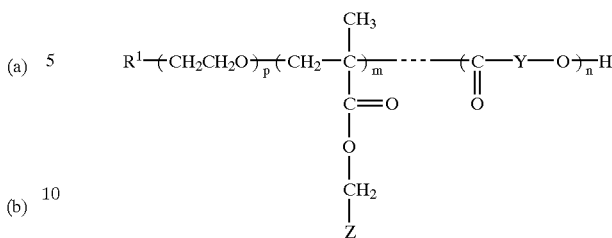

(I-c)

wherein $R^1$, Y, Z, p, m and n are as defined for formula (I), but p is an integer other than 0, can generally form polymer maicelles in which the core consists of segments derived from a methacrylic ester and the shell consists of segments derived from ethylene oxide, when they are stirred in an aqueous medium (e.g., phosphate-buffered physiological saline). Moreover, if a hydrophobic drug, nucleic acid, anionic protein or anionic drug is present in the aforesaid aqueous medium, a polymer micelle in which such a substance is carried by the core can be provided. The polymer micelle thus obtained can be adjusted to an average particle diameter ranging from several nanometers to several hundred nanometers, and hence has characteristics suitable for use as a carrier for the delivery of drugs or as a pharmaceutical composition. Consequently, the polymers of the present invention are also useful as carriers for the delivery of drugs.

The present invention is more specifically explained with reference to the following examples. However, these examples are intended to illustrate the invention, and are not to be construed to limit the scope of the invention.

EXAMPLE 1

Preparation of Poly(N,N-diethylaminoethyl Methacrylate) by Using Potassium Ethoxide as an Initiator

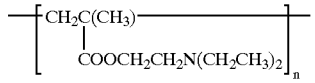

36 mg of potassium ethoxide was accurately weighed into a flask, the atmosphere of which was replaced by argon. 17 mL of tetrahydrofuran and 3.5 mL of N,N-diethylaminoethyl methacrylate were added to the flask, and the resulting mixture was reacted at room temperature for 5 minutes. Analysis by gel permeation chromatography (GPC) revealed that the compound thus obtained was a polymer having a molecular weight of 7,400 and a molecular weight distribution of 1.3. Its NMR chart is shown in FIG. 1. It can be seen from FIG. 1 that the product is poly(N,N-diethylaminoethyl methacrylate) formed by the vinyl polymerization of N,N-diethyl-aminoethyl methacrylate.

EXAMPLE 2

Preparation of Vinylbenzyl-terminated Poly(N,N-diethyl-aminoethyl Methacrylate) Macromonomer

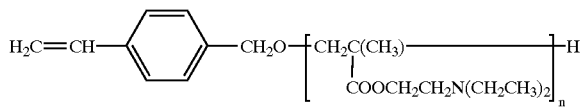

Figure 2:
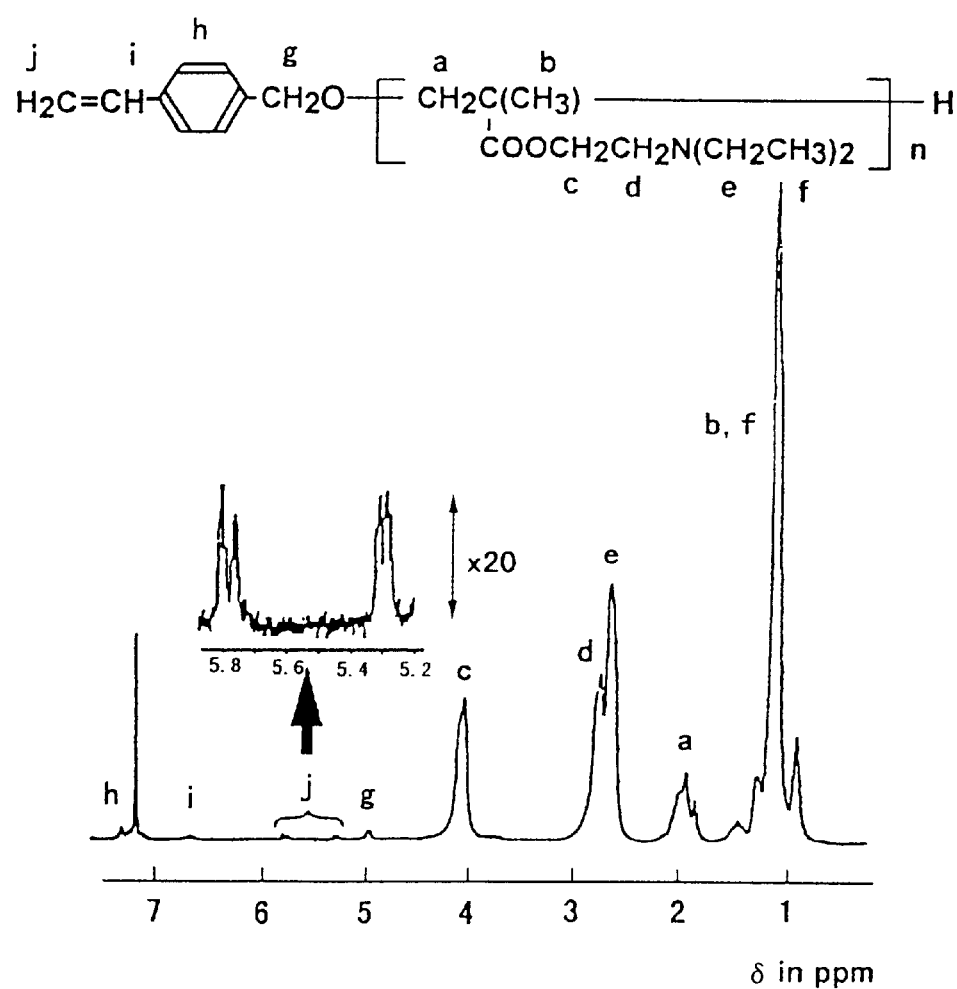
FIG. 2 is an NMR spectrogram of vinylbenzyl-terminated poly(N,N-diethylaminoethyl methacrylate) macromonomer.

Under an atmosphere of argon, 100 mL of THF, 0.3 g of 4-vinylbenzyl alcohol, and 2.5 mL of potassium naphthalene (as a 1 mol/L solution in THF) were added to a flask. After the addition of 20 g of N,N-diethylaminoethyl methacrylate, the resulting mixture was reacted for 5 minutes. Upon analysis by GPC, the quantitatively obtained product had a molecular weight of 8,000 and a molecular weight distribution of 1.2. Its NMR chart is shown in FIG. 2. It can be seen from FIG. 2 that the product is poly(N,N-diethylamino-ethyl methacrylate) macromonomer having a terminal vinylbenzyl group.

EXAMPLE 3

Preparation of Vinylbenzyl-terminated Poly (2-N-benzal-aminoethyl Methacrylate) Macromonomer

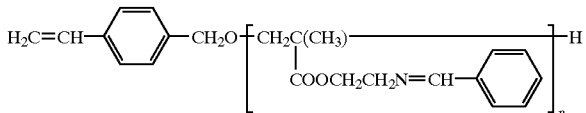

Polymerization was carried out in the same manner as in Example 2, except that 20 g of 2-N-benzalaminoethyl methacrylate was added in place of N,N-diethylaminoethyl methacrylate. Upon analysis by GPC, the quantitatively obtained product had a molecular weight of 8,500 and a molecular weight distribution of 1.2. It was confirmed by its NMR chart that the product was poly(2—N-benzal-aminoethyl methacrylate) macromonomer having a terminal vinylbenzyl group. Moreover, when this polymer was treated with a 0.1N methanolic solution of hydrochloric acid to cleave the imine linkages, there was obtained poly(2-aminoethyl methacrylate) macromonomer.

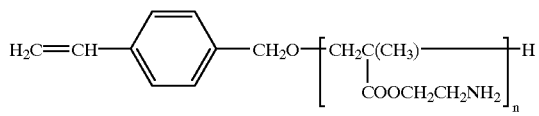

EXAMPLE 4

Preparation of Vinylbenzyl-terminated Poly(2-S-tri-methylsilylmercaptoethyl Methacrylate) Macromonomer

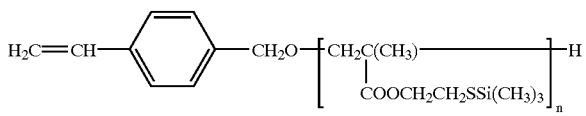

Polymerization was carried out in the same manner as in Example 2, except that 21 g of 2-S-trimethylsilylmercaptoethyl methacrylate was added in place of N,N-diethylaminoethyl methacrylate. Upon analysis by GPC, the quantitatively obtained product had a molecular weight of 9,000 and a molecular weight distribution of 1.2. It was confirmed by its NMR chart that the product was poly(2-S-trimethylsilylmercaptoethyl methacrylate) macromonomer having a terminal vinylbenzyl group. Moreover, when this polymer was treated with tetrabutylammonium fluoride to eliminate the silyl groups quantitatively, there was obtained poly(2-mercaptoethyl methacrylate) macromonomer.

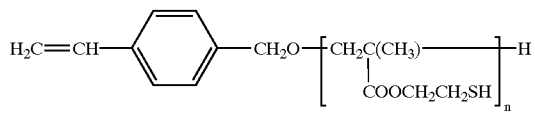

EXAMPLE 5

Preparation of a Copolymer of Poly(N,N-diethylamino-ethyl Methacrylate) and δ-Valerolactone by Using Potassium Ethoxide as an Initiator

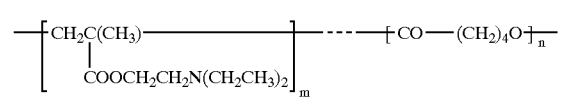

Under an atmosphere of argon, 15 mL of THF, 0.5 g of 4-vinylbenzyl alcohol, and 1.6 mL of potassium naphthalene were added to a flask. After the addition of 2.3 mL (7:10 mmol). of a mixed solution of N,N-diethylaminoethyl methacrylate and δ-valerolactone, the resulting mixture was reacted for 15 minutes. Upon analysis by GPC, the quantitatively obtained product had a molecular weight of 6,000 and a molecular weight distribution of 1.2. It was seen from its NMR chart that the product was a copolymer having a terminal vinylbenzyl group and showing signals attributable to both N,N-diethylaminoethyl methacrylate and δ-valerolactone. When a methanolic solution of a sample of the resulting polymer was poured into a 1N aqueous solution of sodium hydroxide and a molecular weight determination was made by GPC, the copolymer was completely hydrolyzed and oligomers having a molecular weight of the order of several hundred were detected. This clearly indicates that both monomers were not separately polymerized but copolymerized.

EXAMPLE 6

Preparation of a Copolymer of Poly(N,N-diethylamino-ethyl Methacrylate) and ε-Caprolactone by Using Potassium Ethoxide as an Initiator

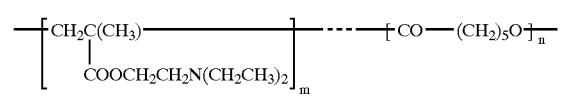

Polymerization was carried out in the same manner as in Example 5, except that ε-caprolactone was used in place of δ-valerolactone. Upon analysis by GPC, the quantitatively obtained product had a molecular weight of 7,000 and a molecular weight distribution of 1.2. It was seen from its NMR chart that the product was a copolymer having a terminal vinylbenzyl group and showing signals attributable to both N,N-diethylaminoethyl methacrylate and ε-caprolactone. Moreover, the results of its alkali hydrolysis was the same as described in Example 5.

EXAMPLE 7

Preparation of an Acetal-poly(ethylene glycol)-poly(N,N-diethylaminoethyl Methacrylate) Block Copolymer

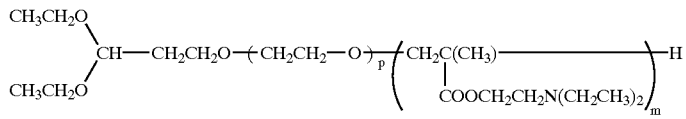

(1) Synthesis

After the atmosphere of an eggplant type flask was replaced by argon, 40 ml of THF as a solvent, 1 mmol (0.16 ml) of 3,3-diethoxy-1-propanol as an initiator, and 1 mmol (3.1 ml) of potassium naphthalene were added thereto. This mixture was stirred for 10 minutes to effect metallization. Thereafter, 100 mmol (5 ml) of ethylene oxide was added thereto and polymerized by stirring for 2 days. During this process, samples were taken from the reaction mixture and analyzed for PEG by GPC. After 20 mmol (3.4 ml) of N,N-diethylaminoethyl methacrylate (DMAEMA) was added thereto and polymerized for 20 minutes, the reaction was stopped by natural 20 deactivation. Subsequently, the product was extracted with chloroform, dehydrated with anhydrous sodium sulfate, filtered, concentrated by evaporation, reprecipitated with ether, filtered by suction, vacuum-dried in a desiccator for a day, and purified by freeze-drying with benzene. The block copolymer thus obtained was analyzed by GPC and $^1$H-NMR spectroscopy.

(2) Separation and Purification 1.1 g of the polymer was dissolved in 40 ml of distilled water, and this solution was adjusted pH 7 by the addition of 0.1N HCl. Then, about 40 ml of an ion-exchange resin (Amberlite, IRC-84) was added thereto, stirred for 30 minutes, filtered by suction, and washed several times with distilled water. Thereafter, the ion-exchange resin was added to an aqueous solution (5 mol/l) of sodium hydroxide, stirred for 30 minutes, filtered by suction, and washed several times with distilled water. After the filtrate was adjusted to pH 10 with 0.1N NaOH and saturated with sodium chloride, the polymer was extracted with chloroform, dehydrated with anhydrous sodium sulfate, filtered, evaporated, and freeze-dried with benzene.

Figure 3:
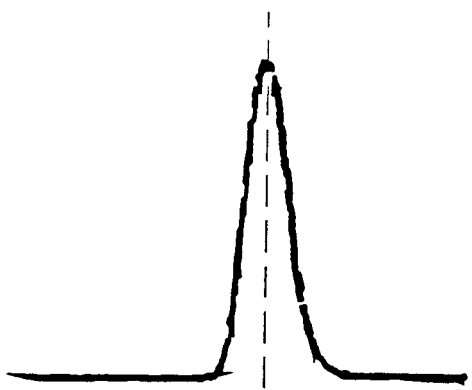
FIG. 3 includes charts showing the results of GPC for (a) the acetal-terminated poly(ethylene glycol) obtained in Example 7, (b) an unpurified sample and (c) a purified sample of the acetal-terminated poly(ethylene glycol)-poly (N,N-diethylaminoethyl methacrylate) block copolymer obtained in Example 7. It is estimated from (a) that Mn=4,900, Mw=5,000, and Mw/Mn=1.04. It is estimated from (b) that Mn=10,500, Mw=11,200, and Mw/Mn=1.07 for the main peak, and Mn=4,700, Mw=4.900, and Mw/Mn=1.03 for the shoulder peak. It is estimated from (c) that Mn=10,700, Mw=12,200, and Mw/Mn=1.07.
Figure 3:
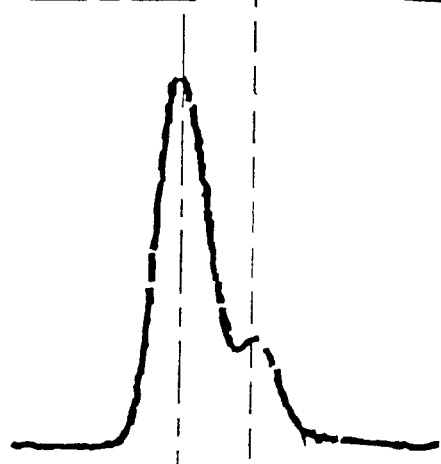
Figure 3:
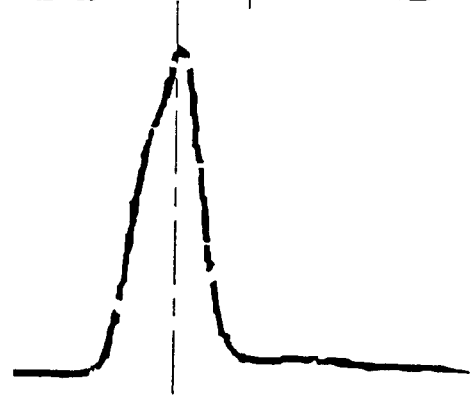
Figure 3:
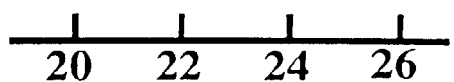

With respect to (a) the polymer (acetal-PEG) sampled after reacting the initiator with ethylene oxide as described above, (b) the acetal—PEG—PDMAEMA obtained after reaction with 10 DMAEMA and before separation and purification, and (c) the acetal-PEG-PDMAEMA obtained after separation and purification, the results of analysis by gel permeation chromatography (GPC) are shown in FIG. 3.

Figure 4:
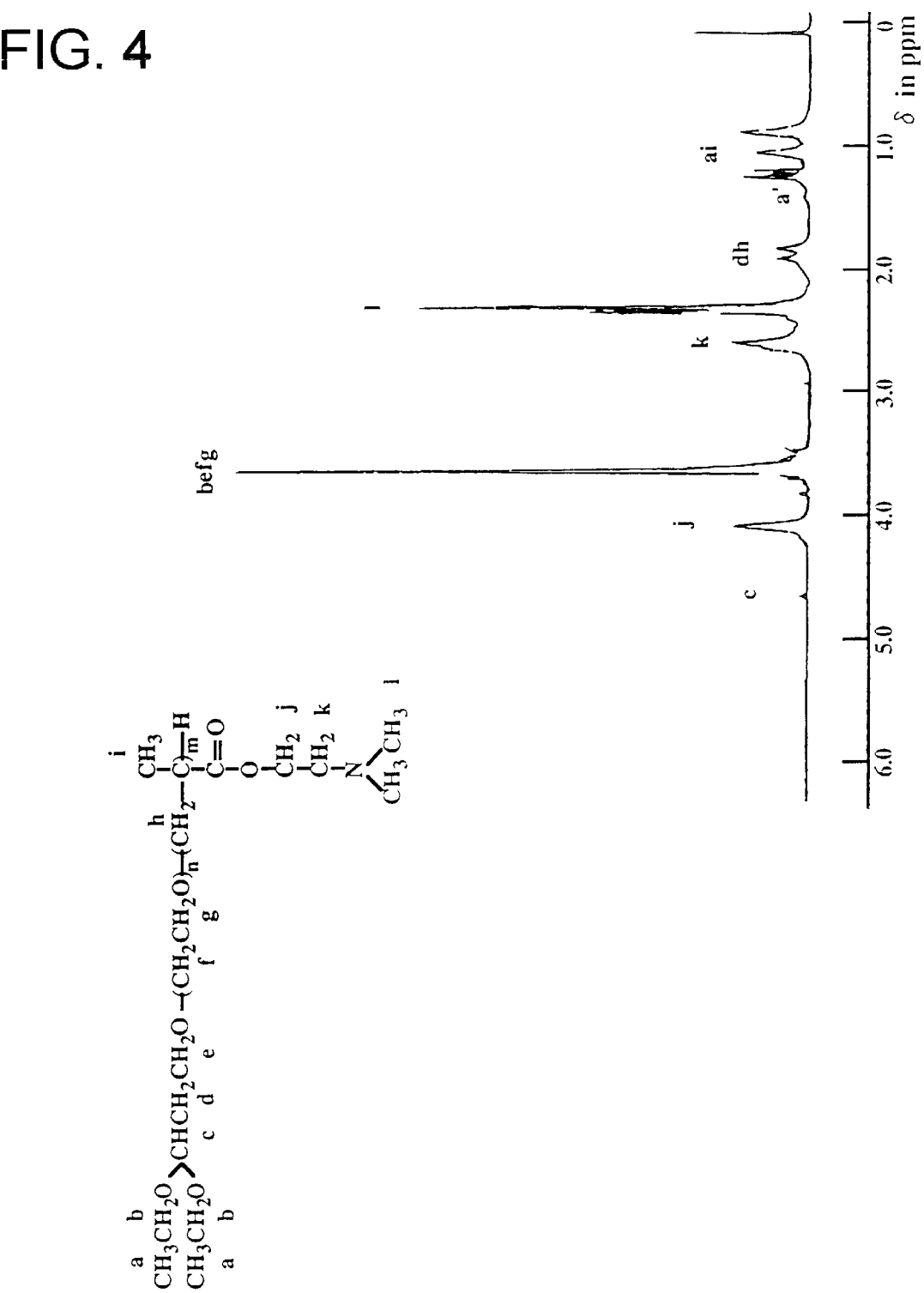
FIG. 4 is an NMR spectrogram of the block copolymer obtained in Example 7.

Moreover, as a result of the aforesaid $^1$H—NMR spectroscopy (solvent: CDCl$_3$, scan: 64, room temperature), an NMR spectrogram is shown in FIG. 4.

EXAMPLE 8

Preparation of Polymer Micelles

Figure 5:
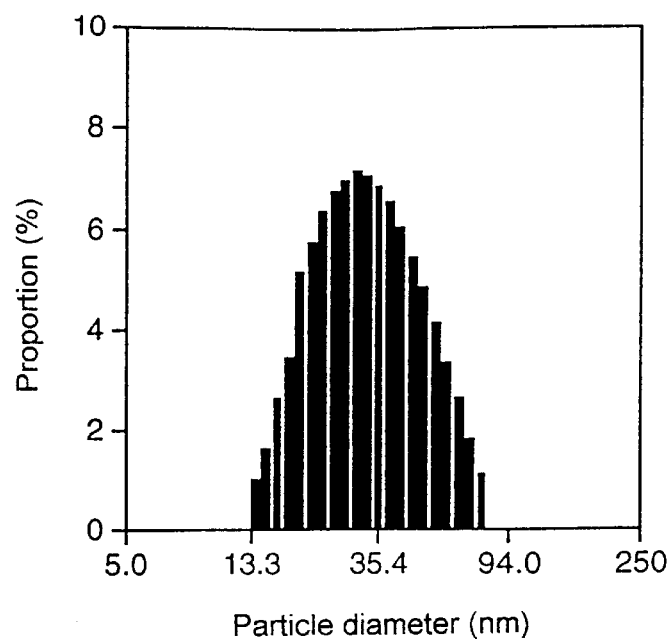
FIGS. 5 and 6 are graphs showing the particle size distribution of the polymer micelles obtained in Examples 8 and 10, respectively.

The acetal-PEG-PDMAEMA block copolymer (having a PEG molecular weight. of 5,000 and containing about 27 dimethylaminoethyl methacrylate units per block copolymer chain; 8.64 mg) obtained in Example 7 after separation and purification was dissolved in a phosphate buffer solution (PBS, 10 mM, pH 7.4, 1.0 ml). The resulting solution was mixed with an aqueous solution of polyvinylsulfuric acid (molecular weight 200,000, 10.0 ml) and allowed to stand at 40° C. overnight. When dynamic light scattering measurements of this solution were made, fine particles having an average diameter of 31.3 nm were detected (the particle size distribution of the micelles is shown in FIG. 5).

EXAMPLE 9

Preparation of Polymer Micelles Freed of the Terminal Protecting Group

An acetal-polyethylene glycol-polydimethylaminoethyl methacrylate block copolymer (having a PEG molecular weight of 5,000 and containing about 27 dimethylaminoethyl methacrylate units per block copolymer chain, 8.64 mg) was dissolved in PBS (1.0 ml), and the resulting solution was mixed with an aqueous solution of polyvinylsulfuric acid (molecular weight 200,000, 10.0 ml). To 3.0 ml of this solution was added 1,2-diamino-4,5-dimethoxybenzene dihydrochloride (0.61 mg) which combines with an aldehyde group to produce fluorescence. Then, this solution was adjusted to pH 2.4 by the addition of 30 μl of 1M hydrochloric acid. Thereafter, its fluorescence spectra (with an excitation wavelength of 338 nm and a fluorescence wavelength range of 350 to 500 nm) were recorded at appropriate intervals of time.

Figure 7:
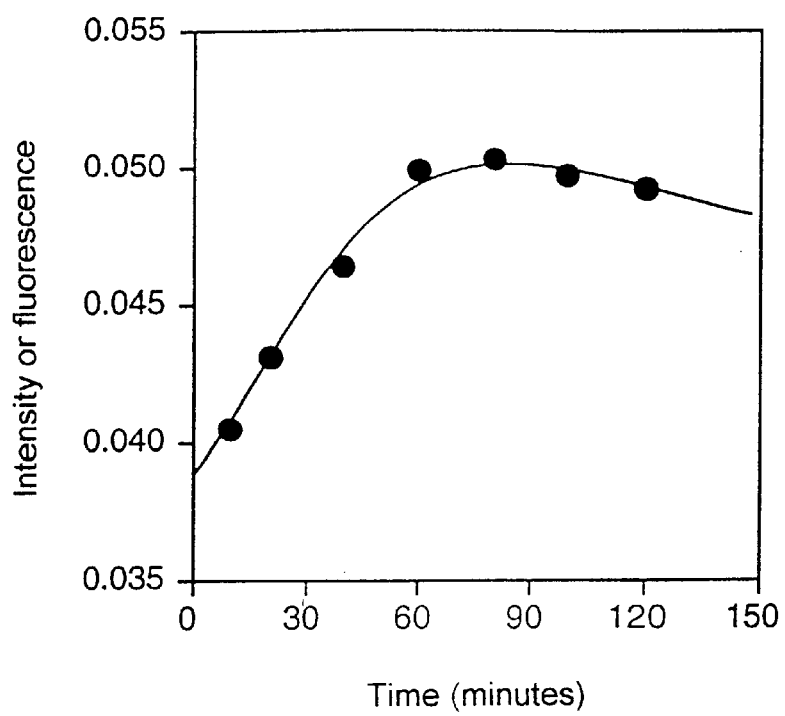
FIG. 7 is a graph showing changes of the reactivity of the aldehyde group with time, as a result of the acetal-to-aldehyde conversion treatment carried out in Example 9.

As a result, it was found that the intensity of fluorescence at 410 nm increased with the lapse of time, indicating that the acetal groups present at the surfaces of the complex were converted to aldehyde groups and that the aldehyde groups present at the surfaces of the complex has reactivity. Changes of the intensity of fluorescence with time are shown in FIG. 7.

EXAMPLE 10

Preparation of Polymer Micelles Freed of the Terminal Protecting Group

Figure 6:
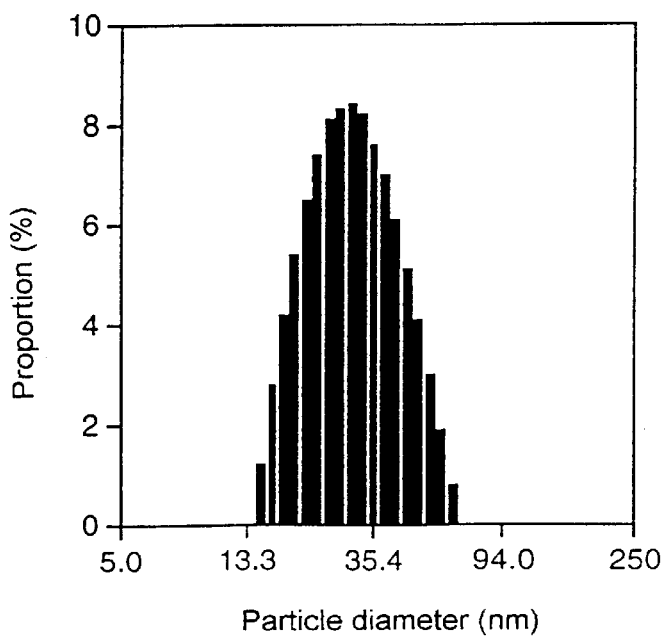

An acetal-polyethylene glycol-polydimethylaminoethyl methacrylate block copolymer (having a PEG molecular weight of 5,000 and containing about 27 dimethylaminoethyl methacrylate units per block copolymer chain, 8.64 mg) was dissolved in PBS (1.0 ml). The resulting solution was mixed with an aqueous solution of polyvinylsulfuric acid (molecular weight 200,000, 10.0 ml), and allowed to stand at 4° C. overnight. 3.0 ml of this solution was taken, adjusted to pH 2.4 by the addition of 30 μl of 1M hydrochloric acid, and stirred for 2 hours to covert the acetal group to an aldehyde group. Then, this solution was adjusted to pH 7.4 by the addition of 1M sodium hydroxide (30 μl). When dynamic light scattering measurements of this solution were made, an average particle diameter of 28.9 nm was detected (the particle size distribution of the micelles is shown in FIG. 6).

EXAMPLE 11

Preparation of Polymer Micelles Containing a Nucleic Acid

An antisense DNA (eicosamer, base sequence: 5'-TGGTGAGGTTTGATCCGCAT-3', 1.0 mg) was dissolved in a tris-hydrochloric acid buffer solution (10 mM, pH 7.4, 1.0 ml), and an acetal-polyethylene glycol-polydimethylaminoethyl methacrylate block copolymer (having a PEG molecular weight of 5,000 and containing about 27 dimethylaminoethyl methacrylate units per block copolymer chain, 1.1 mg) was dissolved in a tris-hydrochloric acid buffer solution (10 mM, pH 7.4, 1.1 ml). These solutions were mixed and allowed to stand at 4° C. overnight. 2.0 ml of this solution was taken, adjusted to pH 2.4 by the addition of 20 µl of 1M hydrochloric acid, and stirred for 2 hours to covert the acetal group to an aldehyde group. Then, this solution was adjusted to pH 7.4 by the addition of 1M sodium hydroxide (20 µl). When dynamic light scattering measurements of this solution were made, an average particle diameter of 87.2 nm was detected.

Exploitability in Industry

The present invention provides polymers which comprise polymethacrylic esters having functional groups in the ester residues thereof and can be prepared by living polymerization. Moreover, these polymers can have another functional group at one end thereof and, at the same time, can be provided in the form of block copolymers or random copolymers. Owing to the properties of the functional groups possessed thereby and their main chain itself, these polymers might be utilized in various fields of industry associated with the surface treatment of a great variety of materials and articles, particularly the manufacture and processing of medical appliances, the production of pharmaceutical preparations, and the like.

What is claimed is:

1. A block copolymer having a hydrophilic polymer segment and hydrophobic polymer segment which has the following formula (I-c'-1)

$$R^1-(CH_2CH_2O)_p-(CH_2-\underset{\underset{\underset{\underset{Z}{|}}{\underset{CH_2}{|}}}{\underset{O}{|}}}{\overset{\overset{CH_3}{|}}{\underset{|}{C}}}-)_m-H$$

wherein:
  $R^1$ is an unsubstituted or substituted straight-chain or branched $C_{1-15}$ alkoxy group, an unsubstituted or substituted aryloxy group, or an unsubstituted or substituted aryl-$C_{1-3}$ alkoxy group, and, when $R^1$ is a substituted group, the substituent is vinyl group; an acetal-forming group which is a substituent on the end carbon atom of the $C_{1-5}$ alkoxy group and is selected from the group consisting of $$(C_{1-6}\text{alkoxyl})_2- \quad \text{and} \quad (CH_2)_S\overset{O}{\underset{O}{\diagdown}}\diagup$$

wherein S is an integer in the range of 1 to 6;
  a cyano group; an aldehyde group; a carboxyl group; an amino group; a $C_{1-6}$ alkoxycarbonyl group; a $C_{2-7}$ acylamide group; a tri($C_{1-6}$alkyl)siloxy group having the same or different alkyl groups; a siloxy group; or a silylamino group;

Z represents the group:

$$-CH_2(CH_2)_rNR^6R^7$$

wherein $R^6$ and $R^7$ are the same or different and represent $C_{1-6}$ alkyl groups, and r is 0 or 1;

p is an integer which is selected such that a polymer micelle can be formed from the copolymer molecules in an aqueous medium and which is not greater than 1,000; and m is an integer in the range of 5 to 10,000.

2. The block copolymer as claimed in claim 1 wherein $R^1$ represents a moiety selected from the group consisting of:

$(CH_3CH_2O)_2CHCH_2CH_2O-$, $(CH_3O)_2CHCH_2CH_2O-$, $(CH_3CH_2CH_2O)_2CHCH_2CH_2O-$, $$\begin{array}{c}CH_2-O\\|\qquad\diagdown\\\quad\quad CHCH_2CH_2O-\\|\qquad\diagup\\CH_2-O\end{array}, \quad \begin{array}{c}CH_2-O\\|\qquad\diagdown\\CH_2\quad CHCH_2CH_2O-\\|\qquad\diagup\\CH_2-O\end{array},$$

$(CH_3CH_2O)_2CH(CH_2)_3O-$, $(CH_3CH_2O)_2CH(CH_2)_4O-$, $(CH_3O)_2CH(CH_2)_3O-$ and $(CH_3O)_2CH(CH_2)_4O-$.

3. The block copolymer as claimed in claim 1 wherein Z represents a group of the formula:

$$-CH_2CH_2NR^6R^7$$

wherein $R^6$ and $R^7$ are the same and represent $C_{1-6}$ alkyl group.

4. The block copolymer as claimed in claim 1 wherein Z represents a group of the formula:

$$-CH_2CH_2N(CH_2CH_3)_2.$$

5. The block copolymer as claimed in claim 1 which has the formula:

$$\begin{array}{c}CH_3CH_2O\\\diagdown\\\quad CH-CH_2CH_2O-(CH_2CH_2-O)_p-(CH_2C(CH_3)\overset{\phantom{|}}{\underset{COOCH_2CH_2N(CH_2CH_3)_2}{|}})_m-H\\\diagup\\CH_3CH_2O\end{array}$$

wherein p and m are as defined for the formula (I-c'-1).

6. A copolymer which is obtained by the process comprising polymerizing a methacrylic ester and a lactone or lactide with an alkali metal alcoholate of the formula (II-c'):

  (II-c')

wherein:

$R^1$ is an unsubstituted or substituted straight-chain or branched $C_{1-15}$ alkoxy group, an unsubstituted or substituted aryloxy group, or an unsubstituted or substituted aryl-$C_{1-3}$ alkoxy group, and, when $R^1$ is a substituted group, the substituent is vinyl group; an acetal-forming group which is a substituent on the end carbon atom of the $C_{1-15}$ alkoxy group and is selected from the group consisting of

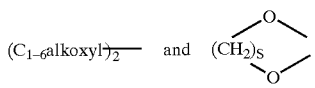

wherein S is an integer in the range of 1 to 6;

a cyano group; an aldehyde group; a carboxyl group; an amino group; a $C_{1-6}$ alkoxycarbonyl group; a $C_{2-7}$ acylamide group; a tri($C_{1-6}$alkyl)siloxy group having the same or different alkyl groups; a siloxy group; or a silylamino group;

and M is lithium, sodium, potassium, cesium or strontium, with a methacrylic ester of the formula (III)

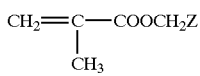 (III)

wherein Z represents the group:

wherein $R^6$ and $R^7$ are the same or different and represent $C_{1-6}$ alkyl groups, and r is 0 or 1;

and optionally with a lactone or lactide of the formula (IV) (a) or (b)

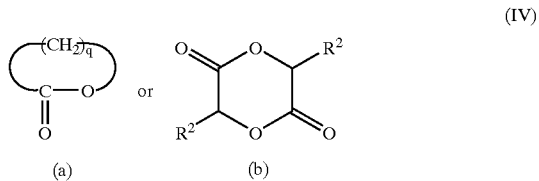 (IV)

(a)          (b)

wherein the $R^2$ groups are the same or different $C_{1-6}$ alkyl groups, and q is an integer in the range of 3 to 5;

optionally in the presence of an inert solvent.

7. The copolymer as claimed in claim 6 wherein $R^1$ represent a moiety selected from the group consisting of:

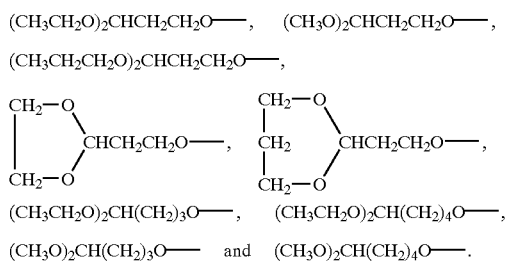

8. The copolymer as claimed in claim 6 wherein Z represents a group of the formula:

wherein $R^6$ and $R^7$ are the same or different and represent a $C_{1-6}$ alkyl group.

9. The copolymer as claimed in claim 6 wherein Z represents a group of the formula:

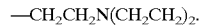

* * * * *